United States Patent [19]

Talma et al.

[11] Patent Number: 5,329,022

[45] Date of Patent: Jul. 12, 1994

[54] PROCESS FOR THE SYNTHESIS OF CITRACONIMIDES

[75] Inventors: Auke G. Talma, Bathmen; Hendrika P. M. Hooft, Soest; Anna G. van de Bovenkamp-Bouwman, Nijkerk, all of Netherlands

[73] Assignee: Akzo America Inc., Chicago, Ill.

[21] Appl. No.: 821,377

[22] Filed: Jan. 16, 1992

[30] Foreign Application Priority Data

Jan. 16, 1991 [EP]  European Pat. Off. ........ 91200076.7

[51] Int. Cl.⁵ .................. C07D 207/44; C07D 403/02; C07D 403/06
[52] U.S. Cl. ..................................... 548/545; 548/521
[58] Field of Search ............................... 548/545, 521

[56] References Cited

U.S. PATENT DOCUMENTS

| | | | |
|---|---|---|---|
| 2,444,536 | 7/1948 | Searle | 260/313 |
| 2,966,498 | 12/1960 | Humphrey | 260/346.8 |
| 4,130,564 | 12/1978 | Haug et al. | 360/326.26 |

FOREIGN PATENT DOCUMENTS

| | | |
|---|---|---|
| 2913300 | 10/1979 | Fed. Rep. of Germany . |
| 62072663 | 9/1985 | Japan . |
| 63196560 | 2/1987 | Japan . |
| 2002378A | 2/1979 | United Kingdom . |

OTHER PUBLICATIONS

Journal of Polymer Science: Polymer Chemistry Ed. vol. 16, No. 1, pp. 137-153 (1978) John Wiley & Sons, Inc.

Journal of Polymer Science: Polymer Chemistry Ed. vol. 19, No. 2, pp. 451-475 (1981) John Wiley & Sons, Inc.

Journal of Polymer Science: Polymer Chemistry Ed. vol. 20, pp. 233-239 (1982) John Wiley & Sons, Inc.

J. Org. Chem., vol. 47, 1572-1574 (1982) American Chemical Society.

Cram and Hammond 2nd Ed. (1964) McGraw Hill, New York, N.Y. p. 362.

*Primary Examiner*—David B. Springer
*Attorney, Agent, or Firm*—Ralph J. Mancini; Louis A. Morris

[57] ABSTRACT

The present invention relates to an improved synthesis method for the making of citraconimides wherein a citraconic anhydride is reacted with 0.5 to 2.0 equivalents of at least one amine salt. This process may be carried out in a solvent and generally leads to excellent yields of the citraconimides with high selectivity and easy purification. The present inventional so relates to a process for the production of citraconic anhydride from itaconic anhydride with an amine or phosphine catalyst and in a cosolvent.

9 Claims, No Drawings

PROCESS FOR THE SYNTHESIS OF CITRACONIMIDES

FIELD OF THE INVENTION

The present invention relates to a process for the synthesis of citraconimides including substituted citraconimides, biscitraconimides, triscitraconimides, tetracitraconimides and oligocitraconimides.

BACKGROUND OF THE INVENTION

Two methods for the production of aliphatic or aromatic bridged biscitraconimides are known. The first method is described in Hartford, S. L., et al., *J. Polym. Sci. Polym. Chem. Ed.*, 16 (1982) 137.

This method begins with itaconic anhydride and an aromatic bis-amine. In a two step reaction the bis-amic acid is ring-closed with sodium acetate and acetic anhydride. The biscitraconimides were formed in low yield of less than 50%, as by-products and were purified by column chromotography.

The second synthesis, found in Galanti, A. V., et al., *J. Polym. Sci., Polym. Chem. Ed.*, 19 (1981) 451 and Galanti, A. V. and Scola, D. A., *J. Polym. Sci, Polym. Chem. Ed.*, 20 (1982) 233, is a one-step reaction from itaconic anhydride to aliphatic bridged biscitraconimides. The itaconic anhydride is reacted with an aliphatic bisamine in toluene to form bis-amic acid, which, under reflux and with azeotropic distillation, forms the imide. The compounds are purified by column chromotography followed by recrystallization. The reaction time is 10–16 hours and the yields are between 17 and 70%.

Both of these known synthesis methods suffer from the problems of poor yields and the requirement of a difficult purification process to isolate the biscitraconimide from the reaction products. Further, the first method is performed under difficult reaction conditions, and the second method takes too long. Thus, there is a need in the art for a better synthesis method for making citraconimides.

In maleimide synthesis, the most frequently employed method is a base-catalyzed synthesis employing either sodium acetate or triethylamine as the base catalyst. These methods are described in U.S. Pat. No. 2,444,536 and U.S. Pat. No. 4,130,564, respectively. One synthesis employing sulfuric acid and an onium salt is disclosed in Japanese patent application J6 2072-663.

However, the maleimide synthesis processes cannot be readily adapted to citraconimide synthesis because, during citraconimide synthesis one is always faced with the problem of isomerization of citraconic molecules to itaconic molecules, a problem which does not exist in maleimide synthesis. This isomerization can lead to low selectivity and poor yields.

Finally, citraconic anhydride is a necessary reactant in the present process. The citraconic anhydride may be obtained commercially, or it may be made by the process described in U.S. Pat. No. 2,966,498, or in Galanti, M. C., Galanti, A. N., *J. Org. Chem.*, 47, 1575 (1982).

However, the foregoing process for making citraconic anhydride suffers from the serious disadvantage that water must be completely removed during the synthesis, by distillation. Thus, the time required to melt the itaconic acid starting material and to completely remove the water is too long for the process to be useful on a commercial scale since, citraconimide polymers begin to form during the distillation. Further, the separated water also gave rise to the formation of citraconic acid, an undesirable by-product.

Thus, there is also a need in the art for a better process for the synthesis of citraconic anhydride, which process provides high yields of the citraconic anhydride without significant polymer formation and allows for simple and economically efficient purification of the citraconic anhydride.

These and other objects of the invention will be apparent to one of ordinary skill in the art from the Summary and Detailed Description which follow.

SUMMARY OF THE INVENTION

The present invention relates to an improved synthesis method for the making of citraconimides wherein a citraconic anhydride is reacted with 0.5 to 2.0 equivalents of at least one amine salt. This process may be carried out in a solvent and generally leads to excellent yields of the citraconimides with high selectivity and easy purification. In a more preferred embodiment of the present invention, said amine salt is formed in situ by the reaction of an amine with an acid. In this manner, inexpensive reactants can be employed for the present production process.

The present invention also relates to a process for the production of citraconic anhydride from itaconic anhydride with a tertiary amine, hindered secondary amine or phosphine and a cosolvent.

The present invention provides advantageous methods for making citraconimides and their precursors. These methods give excellent yields, high selectivity and require straightforward purification processes.

DETAILED DESCRIPTION OF THE INVENTION

The present invention relates to a process for the production of citraconimide, substituted citraconimides, biscitraconimides, tricitraconimides, tetracitraconimides and oligocitraconimides from citraconic anhydride. In this process, the citraconic anhydride is reacted with a salt of an amine with an acid.

The reaction is preferably carried out in a solvent in which the citraconic anhydride is soluble therein and the amine salt is at least slightly soluble therein. Suitable solvents include toluene, xylene, cumene, chlorobenzene, o-dichlorobenzene, decalin, oils and petroleum ethers boiling above 100° C. and mixtures thereof with acids.

The amines used in the process of the present invention may be any amine-containing compound. Of course, the selection of the amine will determine what citraconimide end product will be obtained. Thus, if an aromatic citraconimide is desired, one will employ an aromatic amine. Suitable amines for use in the present process include, but are not limited to, hydrazine, diaminomethane, 1,2-diamino ethane, 1,3-diamino propane, 1,2-diamino butane, 1,2-diamino propane, 1,4-diamino butane, 1,5 diamino pentane, 1,5-diamino(2 methyl)pentane, 1,6-diamino hexane, 1,7-diamino heptane, 1,8-diamino octane, 1,9-diamino nonane, 1,10-diamino decane, 1,12-diamino dodecane, 1,6-diamino-(2,2,3-trimethyl)hexane, isophorone diamine, tricyclo dodecane diamine, m-xylylene diamine, (ortho-, meta- and para) diamino benzene(phenylene diamine), dianiline methane, dianiline ether, dianiline sulphone, 2,2',6,6'-tetraethyl dianiline methane, t-butyl amine, methyl amine, ethyl amine, propyl amine, butyl amine, pentyl amine, hexyl amine, heptyl amine, octyl amine, nonyl amine, decyl amine, octadecyl amine, dodecyl amine, 2-amino ethanol, 3-amino propanol, valine, alanine, glycine, β-alanine, 6-amino hexanoic acid, 1-amino-2-phenyl propane, 3-amino-1,2-propanediol, allyl amine, oleyl amine, 3-chloro-propylamine, furfuryl amine, ammonia, 2,2',6,6'-tetramethyldianiline methane, 2,2'-dimethyl-6,6'-diethyldianiline methane, 2,2',6,6'-tetra-isopropyl dianiline methane, 2,2'-diisopropyl-6,6'-dimethyl dianiline methane, aniline, p-amino benzoic acid, 2-amino-4-methyl phenol, 4-bromo-aniline, 4-amino acetophenone, 4-amino nitrobenzene, 4-amino phenol, 2-amino isopropenylbenzene, benzylamine, aminodiphenylmethane, 1,8-diamino-menthane, 4-aminomethyl-1,8-octane diamine, N-phenyl-1,4-phenylene diamine, 4,4' dianilino diphenylamine, 1-naphthylamine, 2-naphthylamine, 1,8-diamino-3,6-dioxaoctane, 1,5-diamino-3-oxapentane, α,ω-poly tetrahydrofuryl diamines, α,ω-polyglycol diamines (Jeffamines ®), α,ω-polypropoxy diamines (Jeffamines ®), α,ω-polyethoxy-propoxy diamines, 3,5-diamino benzoic acid, 3,4-diamino benzophenone, 1,2-diamino cyclohexane, diamino naphthalene and diamino toluene.

In general, the amine is employed in an amount of 0.5-2.0 equivalents of amine groups per mole of citraconic anhydride. More particularly, it is preferred to use about 0.8-1.2 equivalents of amine groups per mole of citraconic anhydride.

The acid used in the process of the present invention in order to make an amine salt, may be any acid which is soluble in the chosen solvent system. The acids which can be used in the present process include formic, propionic, butyric, pentanoic, hexanoic, oxalic, maleic, acetic, adipic, pivalic, benzoic, toluic, chloroacetic, dichloroacetic and trichloroacetic acids. More particularly, acids such as acetic acid, chloroacetic acid, dichloroacetic acid, trichloroacetic acid and propionic acid, are preferred.

The process of the present invention is generally carried out at a temperature above the melting point of the citraconic anhydride. More particularly, typical reaction temperatures are from 100° to 160° C. Preferably, water is removed during said reaction.

The use of an amine salt in the present process leads to an extremely high yield of the desired citraconimide. The amine salt also provides a higher selectivity and serves to accelerate the reaction, as compared with the same reaction wherein only an amine is employed.

The amine salt may be formed previously or it may be made in situ by mixing an amine with an acid in the solvent system to be used for the reaction. It is always possible, and sometimes advantageous, to employ an amount of acid which is in excess of the amount needed to neutralize the amine. Accordingly, the acid may make up up to 100% of the solvent system and more preferably comprises 40-70%. The amount of acid must be sufficient to neutralize the amino groups and thus 1 to 5 acid equivalents per amino group are generally employed.

The citraconic anhydride used in the present process may be obtained commercially, or it may be made by the process described in U.S. Pat. No. 2,966,498 or in Galanti, M. C. and Galanti, A. N., *J.Org.Chem*, 47, p.1575 (1982).

However, the process for making citraconic anhydride disclosed in U.S. Pat. No. 2,966,498 suffers from the serious disadvantage that water must be completely removed during the synthesis, by distillation. Thus, the time required to melt the itaconic acid starting material and to completely remove the water is too long for the process to be useful on a commercial scale since, citraconimide polymers are formed during the distillation. Further, the separated water also gave rise to the formation of citraconic acid, an undesirable by-product.

In a third aspect, the present invention relates to a process for the production of citraconic anhydride from itaconic anhydride. More particularly, the citraconic anhydride is produced by reacting itaconic acid with acetic anhydride in the presence of a tertiaryamine, or hindered secondary amine or a phosphine, characterized in that the reaction is carried out in a cosolvent.

The cosolvent is a solvent in which the melted itaconic anhydride is readily soluble. Such cosolvents provide significantly better yields of citraconic anhydride and also allow the water of the reaction to be simply and easily removed. Suitable cosolvents include xylene, cumene, o-dichlorobenzene, decalin, citraconic anhydride, toluene, petroleum ethers boiling above 100° C., acetic acid and Shell Ondina ® oil.

The cosolvent may be used in an amount of 0.5 to 3.0% v/v, based on the itaconic acid.

The present invention will be further illustrated by the examples appended hereto.

EXAMPLE 1

Synthesis of Citraconic Anhydride

In a one liter reaction vessel equipped with a thermometer, a mechanical stirrer and a Dean Stark Trap with reflux-condensor, 500 grams of itaconic acid and 10 grams of $NaH_2PO_4$ were suspended in 450 ml of Shell Ondina ® oil. The suspension was warmed very rapidly with an oil bath to 180° C. Upon heating the itaconic acid dissolved/melted and a clear solution was formed from which the water separates. At the end of the water distillation 10-30 ml of xylene was added. When the theoretical amount of water was distilled off, the mixture was cooled and the vessel was equipped with a vacuum distillation set-up.

The xylene was then distilled off at 100° C. and 500 mbar and subsequently the citraconic anhydride was distilled off at 100° C. and 20 mbar. The citraconic anhydride was obtained as a colorless liquid in a 79% yield.

EXAMPLES 2-5

Synthesis of Citraconic Anhydride With Different Solvent

The procedure of Example 1 was followed except that other solvent were substituted for the Shell Ondina ® oil. The solvent used, and the results obtained, are given in Table 1.

TABLE 1

| Example | Cosolvent | Residue (%) | Yield (%) |
|---|---|---|---|
| 2 | Cumene | 11 | 87 |
| 3 | O-dichlorobenzene | — | 90 |
| 4 | Decalin | 11 | 78 |
| 5 | Citraconic Anhydride | 17 | 69 |

COMPARATIVE EXAMPLE 6a

Synthesis of Citraconimide in Toluene

To a solution of 25 mmol of a bisamine in 75 ml toluene, 50 mmol citraconic anhydride was added slowly. The temperature was maintained below 30° C. The bis-amic acid was separated from the reaction mixture. After addition, the reaction was refluxed overnight using a Dean Stark Trap. After cooling the solvent was evaporated. The residue was a white solid. From NMR analysis it was found to be almost quantitatively bis-amic acid. The results are given in Table 2.

EXAMPLE 6

Synthesis of Citraconimide in Toluene

The procedure of Comparative Example 6a was repeated except that 3 equivalents of acetic acid, on the basis of the amine, were added to the toluene. The results are given in Table 2.

COMPARATIVE EXAMPLE 7a

Synthesis of Citraconimide in Xylene

To a well-stirred xylene solution, 50 mmol of citraconic anhydride and 25 mmol of a bisamine were added simultaneously and separately. The bis-amic acid was formed immediately and separated from the solvent. After addition the mixture was refluxed for two hours, using a Dean Stark Trap. The solvent was evaporated under reduced pressure and the crude material was recrystallized from ethanol. The results are given in Table 2.

EXAMPLE 7

Synthesis of Citraconimide in Xylene

The procedure of Comparative Example 7a was repeated except that 3 equivalents of acetic acid, on the basis of the amine, were added to the xylene. The results are given in Table 2.

EXAMPLE 8

The procedure of Example 7 was repeated except that dianiline methane bisamine was employed as the bisamine. The results are given in Table 2.

COMPARATIVE EXAMPLE 8a

The procedure of Comparative Example 7a was repeated except that dianiline methane bisamine was employed as the bisamine. The results are given in Table 2.

TABLE 2

| Example | Solvent | Amine | Acid (3 equival) | Yield (%) | Reaction Time (hrs) |
|---|---|---|---|---|---|
| 6a | Toluene | bisamine | None | 0 | >20 |
| 6 | Toluene | bisamine | Acetic | 91 | 15 |
| 7a | Xylene | bisamine | None | 75 | 3 |
| 7 | Xylene | bisamine | Acetic | 97 | 3 |
| 8a | Xylene | MDA | None | 95 | 15 |
| 8 | Xylene | MDA | Acetic | 97 | 5 |

MDA = Dianiline Methane
Bisamine = 1,6-hexamethylenediamine

EXAMPLES 9-12

The procedure of Example 7 was followed except that four different amines were employed and the yield and degree of isomerization were measured. The results are given in Table 3.

COMPARATIVE EXAMPLES 9a-12a

The procedure of Comparative Example 7a was followed except that four different amines were employed and the yield and degree of isomerization were measured. The results are given in Table 3.

TABLE 3

| | | Without Acetic Acid | | With Acetic Acid | |
|---|---|---|---|---|---|
| Examples | Bis-Citraconimide | Yield (%) | Degree of Isomerization (%) | Yield (%) | Degree of Isomerization (%) |
| 9 | ethylenediamine | 66 | 7 | 95 | 0-1 |
| 10 | 1,6-hexamethylene diamine | 75 | 8-10 | 93 | 0-12 |
| 11 | Dytek A ® | 95 | 10 | 95 | 1-2 |
| 12 | MDACI | 95 | 4-9 | 97 | 0-1 |

MDACI = 4,4'-bis(citraconimide)diphenylmethane
Dytek A ® = 1,5-diamino-2-methylpentane

EXAMPLES 13-15

In these three examples the procedure of Example 7 was followed except that chloroacetic, dichloroacetic and trichloroacetic acids were substituted for acetic acid. The results are given in Table 4.

TABLE 4

| Example | Solvent | Acid | Conversion (%) | Reaction time (hrs) |
|---|---|---|---|---|
| 13 | Xylene | Chloroacetic | 55 | 3 |
| 14 | Xylene | dichloroacetic | 85 | 3 |
| 15 | Xylene | trichloroacetic | 95 | 2.5 |

EXAMPLE 16

Synthesis of Citraconimide in a 1/1 Mixture of Xylene/Acetic Acid

To a solution of 12.36 moles of citraconic anhydride in a mixture of 6 liters of dry xylene and 6 liters of glacial acetic acid at room temperature, 6.18 moles of 1,6-hexamethylene diamine was added at such a rate that the temperature remained below 40° C. During addition, a nice suspension of the bis-amic acid was formed.

After completing the addition, the reaction media was heated to reflux using a Dean Stark Trap. Around 110° C. the azeotrope xylene/acetic acid/water distilled and the solution became clear. The mixture was refluxed for 2-3 hours and after removal of the theoretical amount of water, the solvent was evaporated under reduced pressure. The crude material was recrystallized from either ethanol or methanol.

EXAMPLES 17-22

Synthesis of Citraconimides in a 1 to 1 Mixture of Xylene/Acetic Acid

To a mixture of 3 liters of xylene and 3 liters of glacial acetic acid in a 10 liter reaction vessel equipped with a Dean-Stark Trap, was added 6.18 moles of citraconic anhydride. The mixture was heated to 100°-120° C. To this warm solution was further added 419.75 grams (3.09 moles) of m-xylylene diamine at such a rate that the reflux remained under control. During the addition the water/acetic acid mixture begins to separate from the xylene/acetic acid mixture in the Dean Stark Trap. The addition was carried out over a total period of 15–30 minutes.

At this temperature no suspension of amic acid was formed and after an additional two hours of reflux the theoretical amount of water was removed. The solvent was then evaporated under reduced pressure and the crude material was recrystallized from ethanol or methanol. The results are given in Table 5.

Various amounts of solvent were employed in relation to the amount of product to be produced to demonstrate that the effects are independent of the volume of solvent. The results are given in Table 5.

TABLE 5

| Example | Amount BCI | Amount solvent | Yield (%) | Residual acetic acid | Reactor temp. (°C.) |
|---|---|---|---|---|---|
| 16 | 2 kg | 12 l | 95 | 0.38 | 40 |
| 17 | 1 kg | 6 l | 92 | 0.34 | 100 |
| 18 | 2 kg | 5 l | 93 | 0.76 | 120 |
| 19 | 0.5 kg | 1.2 l | 92 | 0.34 | 110 |
| 20 | 0.5 kg | 1.2 l | 93 | 1.51 | 110 |
| 21 | 1 kg | 1.2 l | 90 | 0.79 | 110 |
| 22 | 1 kg | 0.6 l | 95 | 2.10 | 110 |

EXAMPLE 23

Citraconic Anhydride from Itaconic Anhydride

A suspension of 520 grams (4 moles) of itaconic acid in 500 ml xylene and 408 grams (4 moles) acetic anhydride were heated to 80°–100° C. During the heating the conversion of itaconic acid to itaconic anhydride was almost complete and a clear solution was formed. After ½ hour at 80°–100° C., 0.1% of a tri-propylamine or 0.2% of triphenylphosphine was added and the mixture heated to reflux at 140° C.

Within ½–1 hour the isomerization was completed and the solvents were evaporated under reduced pressure and subsequently the citraconic anhydride was distilled under reduced pressure (25 mbar, 100° C.) to give a colorless liquid in a 79% yield.

EXAMPLES 24–63

To a 3 liter reaction vessel equipped with a mechanical stirrer, a dropping funnel, a thermometer and a Dean-Stark Trap was added 750 ml of glacial acetic acid and acetic anhydride in the amount specified in Table 6. The mixture was heated to 100°–120° C. and a functional primary amine as given in Table 6 was added. In case of sparingly soluble or insoluble amines, a small amount of dimethyl furan was added to increase the solubility of the amine. The mixture was refluxed for 2–3 hours to separate the theoretical amount of water and the solvent was evaporated under reduced pressure. The crude product was either distilled or recrystallized from a suitable solvent.

TABLE 6

| Amine | Amount of Amine (moles) | Amount of Citraconic Anhydride (moles) | Yield (%) | Product |
|---|---|---|---|---|
| Benzylamine | 4.64 | 4.64 | 85.5 | N-benzyl Citraconimide |
| Aniline | 2.67 | 2.67 | 87.8 | N-Phenyl Citraconimide |
| 3-Amino-1,2-propanediol | 2.7 | 2.7 | 100 | N-1,2-propanediol 3-citraconimide |
| Pentylamine | 2.76 | 2.76 | 92.3 | N-pentyl Citraconimide |
| Glycine Methyl Ester* | 2.73 | 2.73 | 56.8 | N-Citraconimido Methyl acetate |
| Glycine | 3 | 3 | 70 | N-citraconimido-2-Acetic Acid |
| β-Alanine | 2.7 | 2.7 | 90 | N-Citraconimido-3-Propionic Acid |
| Allyl Amine | 4.2 | 4 | 86 | N-Allyl Citraconimide |
| Dodecylamine | 1.73 | 1.73 | 95 | N-dodecyl citraconimide |
| Octadecylamine | 1.4 | 1.4 | 100 | N-octadecyl citraconimide |
| Valine | 0.1 | 0.1 | 99 | N-1-Carboxyisobutyl citraconimide |
| 6-amino caproic acid | 0.15 | 0.15 | 95 | N-5-Carboxypentyl citraconimide |
| 2-phenyl propylamine | 0.22 | 0.22 | 88 | N-(2-Methyl-2 phenylethyl) citraconimide |
| ethanol amine | 3.2 | 3.2 | 93 | N-2-hydroxyethyl citraconimide |
| oleyl amine | 0.5 | 0.5 | 90 | N-oleyl citraconimide |
| 3-chloro-propylamine | 0.5 | 0.5 | 100 | N-3-chloropropyl citraconimide |
| ammonium acetate | 0.18 | 0.18 | 76 | Citraconimide |
| 2-amino-p-cresol | 0.46 | 0.46 | 81 | N-2-Hydroxy-5-methyl-phenyl citraconimide |
| 4-bromo aniline | 0.12 | 0.12 | 96 | N-4-Bromophenyl citraconimide |
| p-amino benzoic acid | 0.15 | 0.15 | 97 | N-4-Carboxyphenyl citraconimide |
| p-amino phenol | 0.18 | 0.18 | 97 | N-4-Hydroxyphenyl citraconimide |
| 2-isopropenyl aniline | 0.19 | 0.19 | 96 | N-2-Isopropenylphenyl citraconimide |
| 1,2-diamino ethane | 1.0 | 2.0 | 87 | 1,2-Bis(citraconimido) ethane |
| 1,5-diamino (2-methyl pentane) | 8.2 | 16.4 | ≧98 | 1,5-Bis(citraconimido) |

TABLE 6-continued

| Amine | Amount of Amine (moles) | Amount of Citraconic Anhydride (moles) | Yield (%) | Product |
|---|---|---|---|---|
| 1,6-diamino hexane | 6.6 | 13.3 | 95 | 2-methyl pentane 1,6-Bis(citraconimido) hexane |
| 1,8-diamino octane | 1.0 | 2.0 | 90 | 1,8-Bis(citraconimido) octane |
| 1,10-diamino decane | 1.0 | 2.0 | 92 | 1,10-Bis(citraconimido) decane |
| 1,12-diamino dodecane | 1.0 | 2.0 | 91 | 1,12-Bis(citraconimido) dodecane |
| isophorone diamine | 5.6 | 11.2 | ≧98 | N,N'-Bis(citraconimido) isophorone |
| m-xylylene diamine | 3.09 | 6.18 | 95 | 1,3-Bis(citraconimido-methyl)benzene |
| dianiline methane | 0.7 | 1.4 | 99 | 4,4'-Bis(citraconimido) diphenylmethane |
| m-phenylene diamine | 1.69 | 3.38 | 99 | 1,3-Bis(citraconimido) benzene |
| diamino toluene | 0.15 | 0.3 | 98 | Bis(citraconimido) toluene |
| 1,3-diamino 2,4,6-trimethyl benzene | 0.15 | 0.3 | 93 | 1,3-Bis(citraconimido) 2,4,6-trimethylbenzene |
| 3,5-diamino benzoic acid | 0.15 | 0.3 | 95 | 3,5-Bis(citraconimido) benzoic acid |
| 4,4' methylene bis 2,6 diethyl aniline | 1.0 | 2.0 | 99 | Bis(4-citraconimido-3,5-diethylphenyl) methane |
| 4,4'-methylene-bis-2,6-dimethyl aniline | 0.45 | 0.9 | 90 | Bis(4-Citraconimido-3,5-dimethylphenyl) methane |
| 4-amino diphenyl amine | 0.1 | 0.1 | 90 | N-4-citraconimido diphenylamine |
| 4-aminomethyl-1,8-octane diamine | 1.0 | 3.0 | ≧98 | 1,8-Bis(citraconimido)-4-citraconimidomethyl octane |

*2.73 moles of potassuim acetate were also added to the solvent mix.

What is claimed is:

1. A process for the preparation of citraconimides which comprises reacting citraconic anhydride with 0.5-2.0 equivalents of at least one primary amine salt to form a citraconimide.

2. The process claim 1 wherein said step of producing said citraconimide is carried out in a solvent and said amine salt is at least slightly soluble in said solvent.

3. The process of claim 1 wherein said amine salt is formed in situ by contacting at least one amine with at least one acid.

4. The process of claim 1 further comprising the step of producing said citraconic anhydride by isomerizing itaconic anhydride with a catalytic amount of a tertiary amine, hindered secondary amine or phosphine.

5. The process of claim 4 wherein said isomerization step is carried out in a solvent in which said tertiary amine is soluble.

6. The process of claim 4 further comprising the step of producing said itaconic anhydride by reacting itaconic acid with acetic anhydride in a solvent.

7. The process of claim 1 wherein said amine salt comprises the salt of an amine with acetic acid, propionic acid or a mixture thereof.

8. The process of claim 1 wherein said reaction is carried out in a solvent and in the presence of an amount of an acid in excess of the amount required to form said amine salt.

9. The process of claim 1 wherein said process is carried out at a temperature above 100° C. and water is removed during said reaction.

* * * * *

UNITED STATES PATENT AND TRADEMARK OFFICE
CERTIFICATE OF CORRECTION

PATENT NO. : 5,329,022
DATED : July 12, 1994
INVENTOR(S) : TALMA, Auke et al.

It is certified that error appears in the above—identified patent and that said Letters Patent is hereby corrected as shown below:

Column 9,
In Claim 2, line 1, please insert "of" after "The process".

Signed and Sealed this

Twentieth Day of September, 1994

Attest:

BRUCE LEHMAN

Attesting Officer  Commissioner of Patents and Trademarks